(12) United States Patent
Cheng et al.

(10) Patent No.: US 8,137,520 B1
(45) Date of Patent: Mar. 20, 2012

(54) CHLORIDE ION-SELECTIVE ELECTRODE

(75) Inventors: Chean-Yeh Cheng, Tao-Yuan (TW); Wen-Yaw Chung, Tao-Yuan (TW); Zhu-Ming Huang, Tao-Yuan (TW)

(73) Assignee: Chung Yuan Christian University, Tao-Yuan (TW)

( * ) Notice: Subject to any disclaimer, the term of this patent is extended or adjusted under 35 U.S.C. 154(b) by 0 days.

(21) Appl. No.: 12/969,369

(22) Filed: Dec. 15, 2010

(30) Foreign Application Priority Data

Oct. 13, 2010 (TW) .............................. 99134865 A

(51) Int. Cl.
G01N 27/333 (2006.01)

(52) U.S. Cl. ...................... 204/418; 204/416; 422/82.03

(58) Field of Classification Search .......... 204/416–420; 422/82.03
See application file for complete search history.

(56) References Cited

OTHER PUBLICATIONS

Rothmaier, M., et al., "Response mechanism of anion-selective electrodes based on mercury organic compounds as ionophores", Analytica Chimica Acta, vol. 327, 1996, p. 17-28.*

* cited by examiner

*Primary Examiner* — J. Christopher Ball
(74) *Attorney, Agent, or Firm* — Stout, Uxa, Buyan & Mullins, LLP

(57) ABSTRACT

A chloride ion-selective electrode comprises: a reference electrode in contact with a reference solution; and a chloride ion-selective membrane as the interface of a sample and the reference solution, wherein the chloride-ion selective membrane comprises a chloride ion ionophore, a chloride ion-exchange resin, a plasticizer, and a polymer matrix.

10 Claims, 6 Drawing Sheets

CHLORIDE ION-SELECTIVE ELECTRODE

CROSS-REFERENCE TO RELATED APPLICATIONS

The entire contents of Taiwan Patent Application No. 099134865, filed on Oct. 10, 2010, from which this application claims priority, are incorporated herein by reference.

BACKGROUND OF THE INVENTION

1. Field of the Invention

The present invention relates to chloride ion-selective electrodes.

2. Description of Related Art

Ion-selective electrode (ISE), also known as specific ion electrode (SIE), is a sensor transforming the activity of a specific ion in a solution into electrical potential. The performance of an electrochemical reaction of the ion-selective electrode is in accordance with the Nernst equation. According to the Nernst equation, the transformed potential relates to logarithm of the activity of the specific ion. By sensing the potential of the ion-selective electrode, the activity or concentration of the specific ion can be calculated.

Typically the ion-selective electrode has a sensing portion consisting of an ion-selective membrane and a reference electrode.

Ion-selective electrodes can be used in many fields, such as industry, biochemistry, and environmental protection, for sensing specific ions of solutions. It has many advantages, such as harmless to the tested sample, low limit of detection (LOD), small quantity of sample being required, simple pretreatment process, inexpensive, and easy to measure. However, it has some disadvantages such as low accuracy, measuring activity rather than concentration, and limited lifetime.

Therefore, it would be advantageous to provide a novel ion-selective electrode with quick response time, high accuracy, and long life.

SUMMARY OF THE INVENTION

An object of the present invention is to provide a novel ion-selective electrode with quick response time, high accuracy, and long life.

Accordingly, one embodiment of this invention provides a chloride ion-selective electrode, for sensing the concentration of chloride ion of a sample solution. The chloride ion-selective electrode comprises a reference electrode immersed in a reference solution containing chloride ions, and a chloride ion-selective membrane, as an interface of the sample solution and the reference solution. The chloride ion-selective membrane comprises a chloride ionophore for binding chloride ions, a chloride ion-exchange resin for exchanging chloride ions of the sample solution and the reference solution, a plasticizer, and a polymer matrix.

DESCRIPTION OF THE PREFERRED EMBODIMENT

Figure 1:
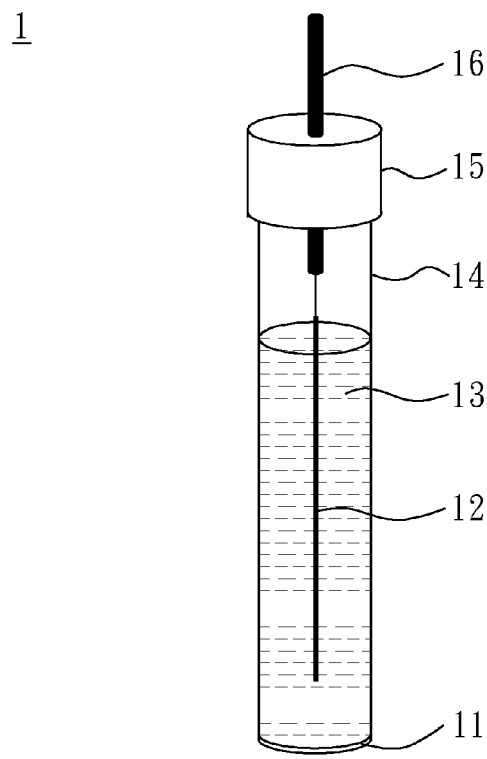
FIG. 1 shows a chloride ion-selective electrode 1 according to an embodiment of this invention.

Reference will now be made in detail to specific embodiments of the invention. Examples of these embodiments are illustrated in accompanying drawings. While the invention will be described in conjunction with these specific embodiments, it will be understood that it is not intended to limit the invention to these embodiments. On the contrary, it is intended to cover alternatives, modifications, and equivalents as may be included within the spirit and scope of the invention as defined by the appended claims. In the following description, numerous specific details are set forth in order to provide a thorough understanding of the present invention. The present invention may be practiced without some or all of these specific details. In other instances, well-known process operations and components are not described in detail in order not to unnecessarily obscure the present invention. While drawings are illustrated in detail, it is appreciated that the quantity of the disclosed components may be greater or less than that disclosed, except where expressly restricting the amount of the components. Wherever possible, the same or similar reference numbers are used in drawings and the description to refer to the same or like parts.

The following example illustrates how to produce a chloride ion-selective electrode according to an embodiment of this invention; however, the chloride ion-selective electrode may be produced by other methods in other embodiments.

Example to Produce a Chloride Ion-Selective Membrane

First, a chloride ion-exchange resin, in the form of pellets, such as pellets of Trimethyl ethenyl quarternary ammonium chloride polystyrene-divinylbenzene resin (TMEQAC PSDVB resin, CAS Number: 60177-39-1), is placed in an oven to be dehydrated at 50° C. for 24 hours. Then the chloride ion-exchange resin pellets are grinded to white powders by a pulverizer for 5 times and the duration of each time is 60 seconds. The white powders are stored in a vacuumed and humidity-controlled box for later use.

Then, take 5.0 mg of white powders of the chloride ion-exchange resin to add it in a vessel contained 5.0 mL of tetrahydrofuran (THF). A mixer is used to shake the vessel for 3 minutes and make the chloride ion-exchange resin solution in the vessel limpid. Take 0.1 mL of the chloride ion-exchange resin solution to add in another vessel contained 0.9 mL tetrahydrofuran (THF). Again the vibrator is used to vibrate the later vessel for 3 minutes and make the chloride ion-exchange resin solution limpid. By doing so, the chloride ion-exchange resin solution is diluted to 0.1 mg/mL.

Then, prepare an ion-selective membrane solution, which comprises an ion ionophore, a plasticizer, a polymer matrix, and a solvent. In this example, the ion ionophore is {μ[4,5-dimethyl-3,6-bis(dodecyloxy)-1,2-phenylene]} bis(mercury chloride) (ETH9033, CAS Number 178959-28-9), the plasticizer is (bis(2-ethylhexyl)sebacate (DOS, CAS Number 122-62-3), the polymer matrix is polyvinyl chloride (PVC), and the solvent is tetrahydrofuran (THF). In another embodiment, polyethylene glycol (PEG) may be used as the polymer matrix. For preparing the ion-selective membrane solution, first, take 2.2 mg of the ionophore (ETH9033), 71.19 mg of the plasticizer (DOS), 33.26 mg of the polymer matrix (PVC), and 740 µL of the solvent (THF) and mix them to a solution, wherein the weight ratio of the ion ionophore, the plasticizer, the polymer matrix, and the solvent is about 2:67:31. Then, add 260 µL of the above prepared 0.1 mg/mL of chloride ion-exchange resin solution into the above solution, wherein the weight ratio of the ion ionophore (2.2 mg, ETH9033) to the chloride ion-exchange resin (0.026 mg) is about 99:1. The mixed solution is then mixed by the mixer for 6 minutes to make it limpid. The limpid solution is the desired ion-selective membrane solution. The ion-selective membrane solution is then poured in a glass ring (28 mm i.d., 30 mm ht) of a glass plate, which is then placed into the oven to evaporate the solvent at 30° C. for 24 hours. After the solvent is evaporated, a chloride ion-selective membrane is formed.

Notice that in other embodiments of this invention, the weight ratio of the composition may be varied.

Example to Produce a Chloride Ion-Selective Electrode

FIG. 1 shows a chloride ion-selective electrode 1 according to an embodiment of this invention. The chloride ion-selective electrode 1 comprises major components including an ion-selective membrane 11, a reference electrode 12, and a reference solution 13, and comprises minor components including a body 14, a lid 15, and a wire 16. These minor components may be omitted or modified in other embodiments of this invention. In this embodiment, a ring-shaped cutter cuts the above formed chloride ion-selective membrane to form a round-shaped membrane with diameter 8.0 mm. The round-shaped ion-selective membrane is then placed in front end of the body 14 and arranged between the reference solution 13 and a sample solution (not shown). The reference solution 13 may comprise 0.1 M of potassium chloride (KCl) solution filling the cannulation of the body 14. The body 14 may be made of glass, plastic, stainless steel, or other suitable materials and it may be tubular, cannular, or other suitable shapes. The reference electrode 12 may comprise silver/silver chloride (Ag/AgCl) electrode arranged in the reference solution 13, transmitting the potential to a test system (not shown) via the wire 16. In addition, the lid 15 seals the other end of the body 14.

The produced chloride ion-selective electrode 1 may be stored in a 0.01 M of KCl solution when not in use. The KCl solution for storing the electrode should be replaced by another fresh one to aid the electrode in long-term use.

On-Line Real Time Test System

Figure 2:
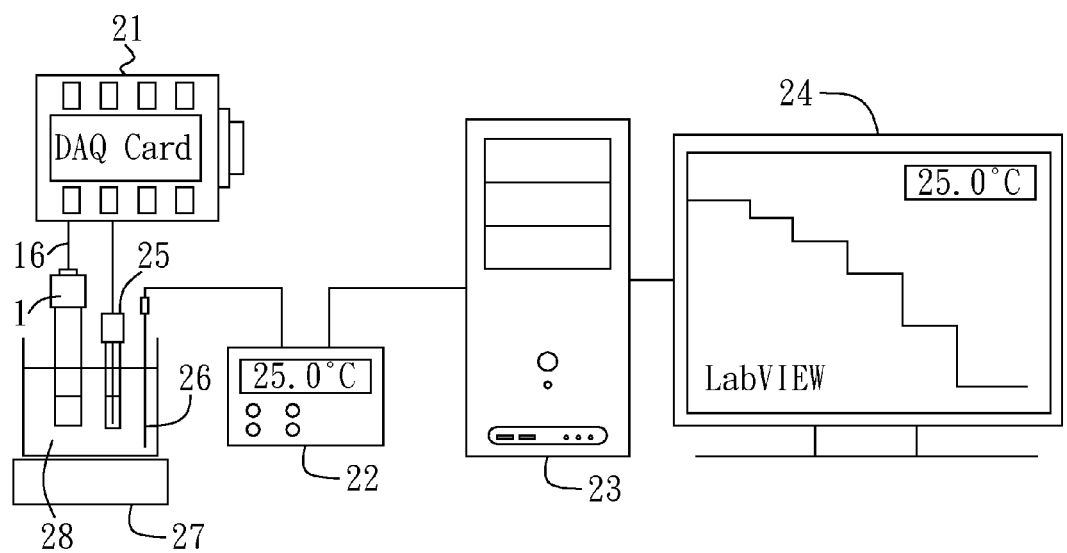
FIG. 2 shows the developed chloride ion-selective electrode of FIG. 1 being used in an on-line real time test system, for measuring concentration of chloride ions in a sample solution.

FIG. 2 shows the developed chloride ion-selective electrode being used in an on-line real time test system, for measuring concentration of chloride ions in a sample solution. As shown in FIG. 2, a test system 2 includes: a chloride ion-selective electrode 1 and an outer reference electrode 25 for contacting with a sample solution 28; a data acquisition system 21, such as commercial data acquisition (DAQ) card sold by National Instruments Corporation, Austin, Tex., USA, acquiring the potential by connecting the chloride ion-selective electrode 1 and the outer reference electrode 25 via the wires 16; temperature acquisition system 22, acquiring temperature of the sample solution 28 via the temperature probe 26; a computer 23 with a data-processing system 24, such as LabVIEW commercial software sold by National Instruments Corporation, processing the acquired potential and temperature; an agitation system 27, such as magnetic stirrer, agitating the sample solution 28 to make the solution homogeneous.

Limit of Detection of the Developed Chloride Ion-Selective Electrode

Figure 3:
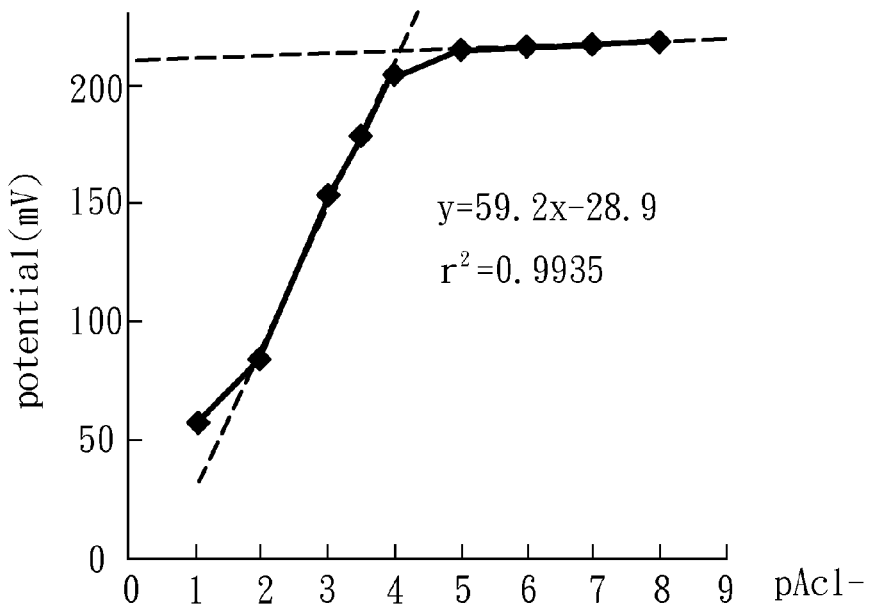
FIG. 3 shows a standard addition calibration curve of nine standard NaCl solutions measured by a developed chloride ion-selective electrode of this invention.

The standard addition method is used to determine the activity (concentration) of chloride ion in an unknown sample solution. By using sodium chloride (NaCl) standard sample, nine standard NaCl solutions with $pA_{Cl-}(=-\log A_{Cl-})$ equal to 8.02, 7.00, 6.00, 4.99, 4.00, 3.50, 3.00, 2.00, and 1.06 are prepared. The developed chloride ion-selective electrode is used to perform the quantitative analysis of the nine standard solutions at 25° C. FIG. 3 shows a typical standard addition calibration curve of the nine standard solutions, which can be divided into a linear sensing section (y=59.2x−28.9) at higher activities and a poor sensing section at lower activities. The former has a slope of 59.2 mV/decade the same as the ideal slope of the Nernst equation. The x-coordinate of the intersection of the two sections is the limit of detection for chloride ion. The ionic strength of the standard solutions is used to calculate the activity coefficient ($\gamma$), which is turned to the unit of molar concentration (M) or parts per million (ppm) through the equation $A_{Cl-}=\gamma[Cl^-]$. After conversion, the limit of detection of the developed chloride ion-selective electrode is 2.5 ppm.

Response Time of the Developed Chloride Ion-Selective Electrode

Figure 4:
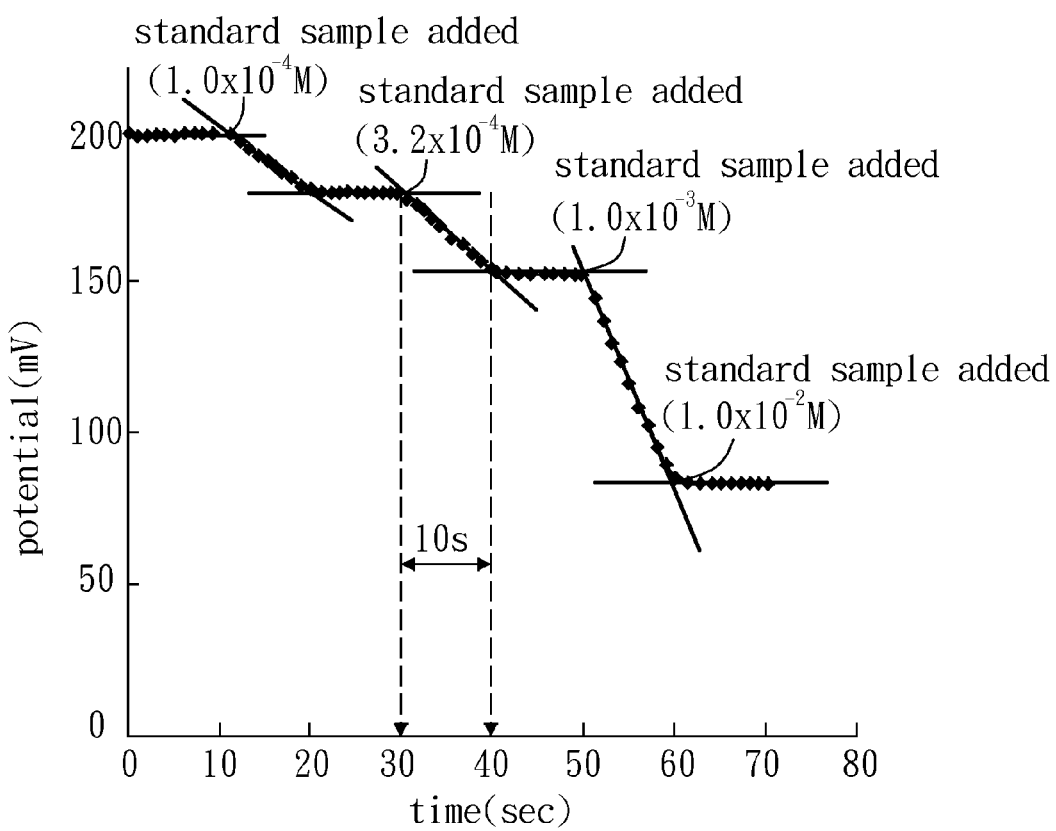
FIG. 4 shows the response time of a developed chloride ion-selective electrode of this invention.

FIG. 4 shows the response time of the chloride ion-selective electrode of this invention. Four NaCl standard solutions with different concentration are separately added to a sample solution under test and the measured potential will be changed. The time needed to the steady potential for each addition is thus the response time. As shown in FIG. 4, the response time of the developed chloride ion-selective electrode is about 10 seconds. The short response time is helpful to apply the electrode in the on-line real time measuring system.

The selectivity coefficient of the developed chloride ion-selective electrode The separate solution method (SSM, Y. Umezawa, P. Bühlmann, K. Umezawa, K. Tohda, S. Amemiya, "Potentiometric selectivity coefficients of ion-selective electrode," Pure and Applied Chemistry, 72 (2000) 1851-2082) is used to determine the selectivity coefficient of non-chloride ions of the developed chloride ion-selective electrode. The higher is the selectivity coefficient; the lower is the extent of interfering. Table 1 shows the selectivity coefficients of some interfering ions of the developed chloride-ion selective electrode. The developed chloride-ion selective electrode has good selectivity coefficients for common anions, such as nitrate ion ($NO_3^-$), sulfate ion ($SO_4^{2-}$), and carbonate ion ($CO_3^{2-}$), and most of other anions show low or free of interfering extent.

TABLE 1

| Compound | Interfering ion | Selectivity coefficient ($-\log K_{ClB}^{Pot}$) |
|---|---|---|
| NaF | $F^-$ | 6.6 |
| NaBr | $Br^-$ | 1.3 |
| NaI | $I^-$ | 0.8 |
| KSCN | $SCN^-$ | 0.2 |
| $KNO_3$ | $NO_3^-$ | 4.5 |
| $NaHCO_3$ | $HCO_3^-$ | 3.6 |
| $CH_3COONH_4$ | $CH_3COO^-$ | 4.8 |
| $NaNO_2$ | $NO_2^-$ | 1.8 |
| $NaClO_4$ | $ClO_4^-$ | 3.0 |
| $KMnO_4$ | $MnO_4^-$ | 0.8 |
| $Na_2S$ | $S^{2-}$ | 2.5 |
| $K_2HPO_4$ | $HPO_4^{2-}$ | 5.1 |
| $Na_2SO_4$ | $SO_4^{2-}$ | 4.2 |

TABLE 1-continued

| Compound | Interfering ion | Selectivity coefficient ($-\log K_{Cl,B}^{pot}$) |
|---|---|---|
| $Na_2SO_3$ | $SO_3^{2-}$ | 3.1 |
| $Na_2CO_3$ | $CO_3^{2-}$ | 4.2 |
| $K_2CrO_4$ | $CrO_4^{2-}$ | 5.5 |

The Lifetime and Stability of the Developed Chloride Ion-Selective Electrodes

Figure 5:
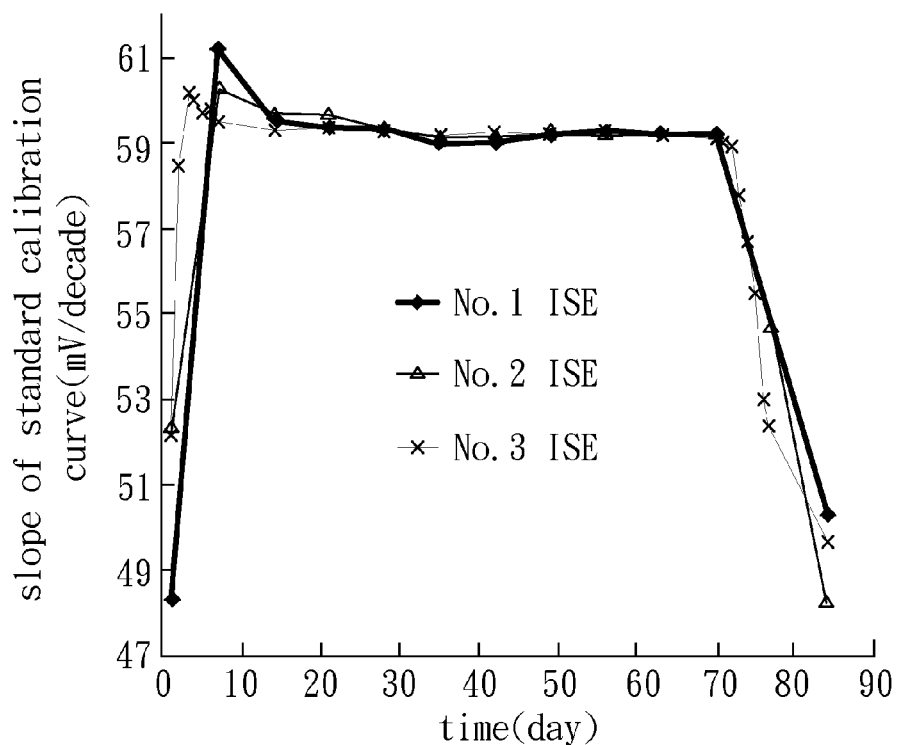
FIGS. 5-7 respectively show the variation of slopes, linear correlation coefficients ($r^2$), and limit of detections (LODs) of the standard addition calibration curves of the developed chloride ion-selective electrodes (ISEs) under long-term operation.
Figure 6:
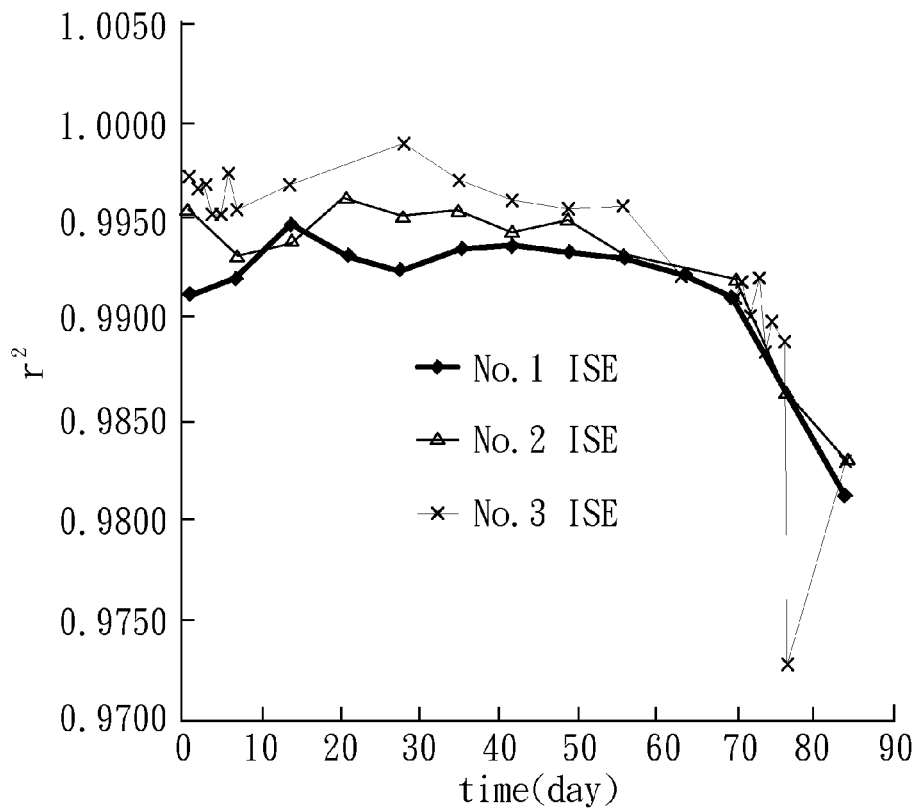
Figure 7:
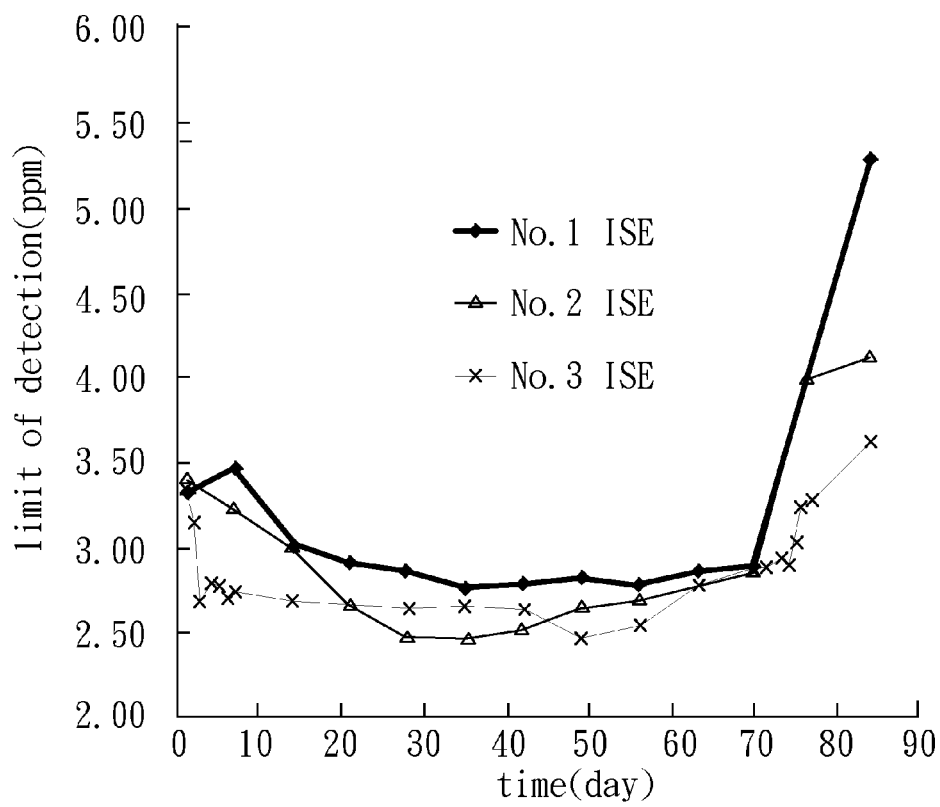

FIGS. 5-7 respectively show the variation of slopes, linear correlation coefficients ($r^2$), and limit of detections (LODs) of the standard addition calibration curves of the developed chloride ion-selective electrodes (ISEs) under long-term operation. The linear concentration ranges of all ISEs are fixed between $1.0 \times 10^{-4}$ and $1.0 \times 10^{-2}$ M. In addition, different chloride ion-selective electrode may have different thickness of ion-selective membrane.

As shown in FIG. 5, the no. 2 chloride ion-selective electrode had a slope 52.2 mV/decade initially, turned to 60.3 mV/decade at the seventh day, and fixed about 59.2 mV/decade since the fourteenth day to the seventieth day. The slope 59.2 mV/decade just meets the ideal slope of the Nernst equation. The other two ISEs also show similar features.

As shown in FIG. 6, all linear correlation coefficients ($r^2$) of the standard addition calibration curves of the developed ISEs are more than 0.9910 till the seventieth day. This indicates that the developed ISEs of this invention reveal good linearity at the concentration range between $1.0 \times 10^{-4}$ and $1.0 \times 10^{-2}$ M.

As shown in FIG. 7, all limit of detections (LODs) of the standard addition calibration curves of the developed ISEs are kept between about 2.5 ppm and 3.5 ppm. Particularly, the limit of detection of the no. 3 ISE keeps between about 2.50 to 2.80 ppm since the third day to the seventy-fifth day.

FIGS. 5-7 prove that the lifetime and stability of the developed chloride ion-selective electrodes of this invention can reach 70 days or more.

Temperature Effect to the Developed Chloride Ion-Selective Electrodes

Figure 8:
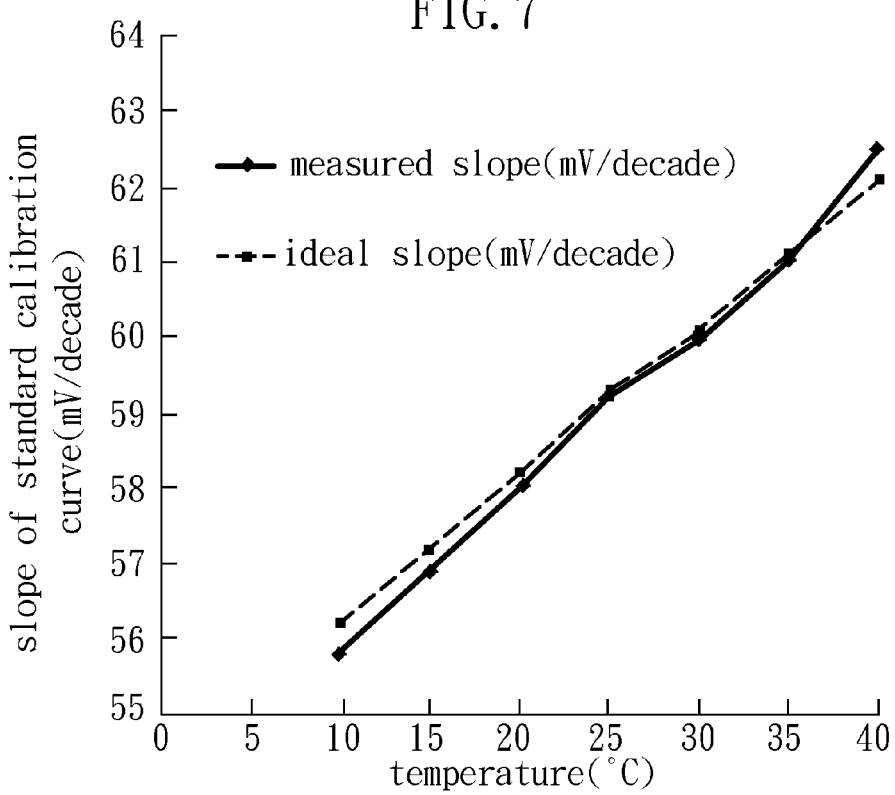
FIG. 8 shows the temperature effect on a developed chloride-ion selective electrode of this invention.

FIG. 8 shows the temperature effect on a developed chloride-ion selective electrode. Under various temperatures including 10, 15, 20, 25, 30, 35, 40, and 45° C., standard addition calibration curves of the chloride-ion selective electrode are separately prepared and the slopes of the prepared standard addition calibration curves are compared to the ideal slope of Nernst equation, as shown in FIG. 8. The result shows that the deviation between the slope of the developed ISE and the ideal slope is less than 0.7% at different temperatures. This indicates that the developed chloride ion-selective electrode can be used in a wide temperature range.

pH Effect on the Developed Chloride Ion-Selective Electrodes

Figure 9:
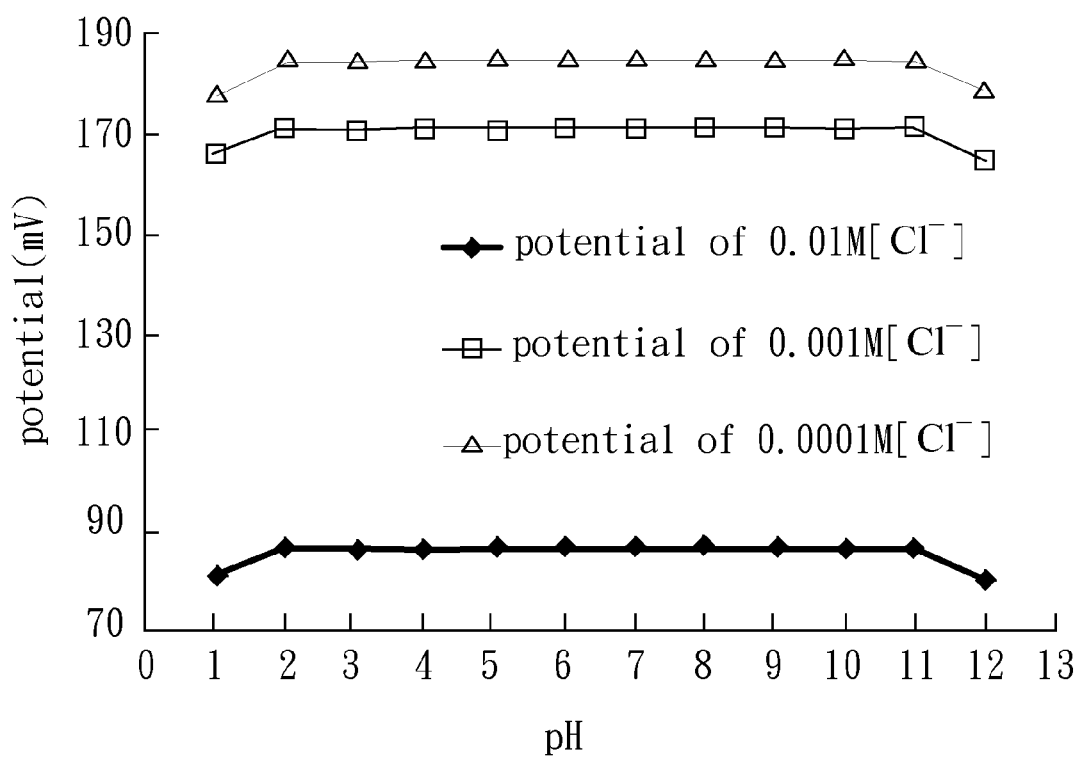
FIG. 9 shows the working pH range of the developed chloride ion-selective electrode of this invention.

FIG. 9 shows the working pH range of the developed chloride ion-selective electrode of this invention. Thirty-six chloride ion solutions, with a variety of pH from 1.0 to 12.0 and three different concentrations $1.0 \times 10^{-2}$, $1.0 \times 10^{-3}$, and $1.0 \times 10^{-4}$ mol $L^{-1}$, are separately prepared by using chloride standard solution, sulfuric acid ($H_2SO_4$), and sodium hydroxide (NaOH). The thirty-six chloride solutions are then tested to understand the pH effect. As shown in FIG. 9, the chloride ion solutions at the same concentration reveal about the same measured potential in the range from pH 2.0 to pH 11.0. When pH is less than 2.0 or more than 11.0, the measured potential decayed due to the interfering of sulfate ion ($SO_4^{2-}$) and hydroxyl ion (OH), respectively.

The Accuracy of the Developed Chloride Ion-Selective Electrode

To check the accuracy, both the developed chloride ion-selective electrode and HPLC are used to determine the concentration of chloride ion in some unknown samples. A statistical t-test is employed to determine if a difference of the quantitative results is present between the two analytical methods. The samples are obtained from groundwater, dam water, and rainwater. Table 2 lists the test result. With 95% confidence interval, t-test judges that the measured results of the two methods are the same.

In addition, the accuracy of the developed ISE for each sample is estimated by a spike experiment and is calculated between 92% and 95%, as listed in Table 2.

TABLE 2

| Sample | Developed ISE[a] | HPLC[b] | t-test (95% confidence interval) | Accuracy % |
|---|---|---|---|---|
| groundwater | 20.7 ± 0.5 ppm | 20.9 ± 0.1 ppm | the same | 92 |
| dam water | 13.2 ± 0.4 ppm | 12.9 ± 0.1 ppm | the same | 93 |
| rainwater | 4.5 ± 0.2 ppm | 4.6 ± 0.1 ppm | the same | 95 |

[a]. Times of measurement = 5 (n = 5).
[b]. Times of measurement = 4 (n = 4).

Table 3 lists the performance and the composition of the ion-selective membrane of the developed ISE (data listed in the first row) and some other ISEs from literatures (data listed in the second row to the fifth row, which are respectively obtained from M. Rothmaier, U. Schaller, W. E. Morf, E. Pretsch, "Response mechanism of anion-selective electrodes based on mercury organic compounds as ionophores," Analytica Chimica Acta, 327 (1996) 17-28; K. P. Xiao, P. Bühlmann, S, Nishizawa, S. Amemiya, Y. Umezawa, "A Chloride Ion-Selective Solvent Polymeric Membrane Electrode Based on a Hydrogen Bond Forming Ionophore," Analytical Chemistry, 69 (1997) 1038-1044; D. Tonelli, I. Carpani, L. Mazzocchetti, L. Angiolini, D. Caretti, E. Salatelli, F. Tarterinic, "Novel Poly(ethylene glycol)s Bearing Tributyltin Carboxylate EndGroups as Ionophores in the Development of Chloride Ion-Selective Electrodes," Electroanalysis, 18 (2006) 1055-1062; E. D. Steinle, U. Schaller, M. E. Meyerhoff, "Response Characteristics of Anion-Selective Polymer Membrane Electrodes Based on Gallium(III), Indium(III) and Thallium(III) Porphyrins," Analytical Sciences, 14 (1998) 79-84.)

TABLE 3

| Composition of ion-selective membrane | | | | Potentiometric parameters | | | | | |
|---|---|---|---|---|---|---|---|---|---|
| ionophore | ion-exchanger | plasticizer | polymer matrix | slope (mV/decade) | limit of detection (M) | linear concentration range (M) | $r^2$ | response time (s) | lifetime (day) |
| ETH 9033 | TMEQAC PSDVB resin | DOS | PVC | 59.2 | $6.9 \times 10^{-5}$ | $1.0 \times 10^{-2}$-$1.0 \times 10^{-4}$ | 0.9957 | 10 | 70 |
| ETH 9033 | TDDMACl | DOS | PVC | 56.9 | — | $1.0 \times 10^{-1}$-$1.0 \times 10^{-5}$ | — | 16 | — |

TABLE 3-continued

| Composition of ion-selective membrane | | | | Potentiometric parameters | | | | | |
|---|---|---|---|---|---|---|---|---|---|
| ionophore | ion-exchanger | plasticizer | polymer matrix | slope (mV/decade) | limit of detection (M) | linear concentration range (M) | $r^2$ | response time (s) | lifetime (day) |
| Bis-thiourea | TDDMACl | α-NPOE | PVC | 54.0 | $6.5 \times 10^{-6}$ | $1.0 \times 10^{-2}$-$1.0 \times 10^{-5}$ | — | — | 28 |
| Tributyltin carboxylate | TDDMACl | α-NPOE | PEG | 47.0 | — | $1.0 \times 10^{-2}$-$1.0 \times 10^{-4}$ | 0.9975 | 25 | 7 |
| Ga(III)[OEP]Cl | TDDMACl | α-NPOE | PVC | 57.0 | — | $2.5 \times 10^{-2}$-$1.0 \times 10^{-5}$ | — | 50 | 30 |

As shown in Table 3, the developed ISE of this invention reveals a slope nearest to the slope of Nernst equation, and reveals the shortest response time and the longest lifetime.

Figure 10:
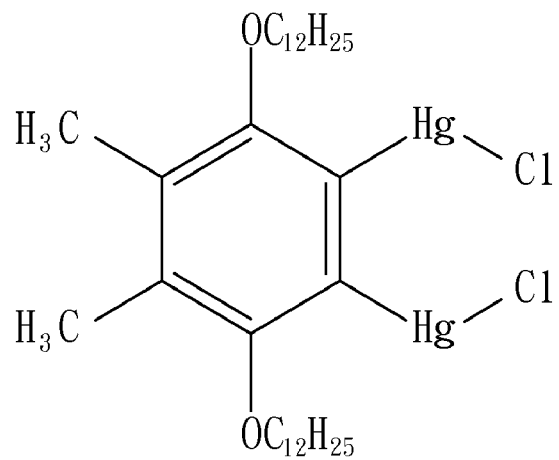
FIG. 10 shows the structure of the ionophore ETH9033.
Figure 11:
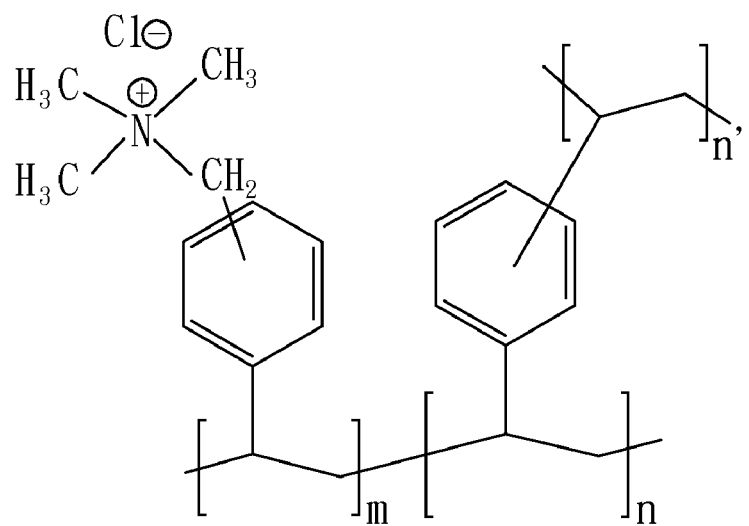
FIG. 11 shows the structure of the chloride ion-exchange resin used in a preferred example of this invention, trimethyl ethenyl quarternary ammonium chloride polystyrene-divinylbenzene resin.

According to embodiments of this invention, the ion-selective membrane of the developed chloride ISE consists of an ionophore, an ion-exchanger, a plasticizer, and a polymer matrix. In the foregoing embodiment, ETH9033 is used as the ionophore, whose molecular structure is shown in FIG. 10. The benzene ring derivative has two ortho-positions individually arranged with a mercury atom, and each mercury atom can bind a chloride ion. Because the binding force between mercury atom and chloride ion is greater than other anions, ETH9033 has good selectivity for chloride ion. Instead of ETH9033, other ionophores such as bis-thiourea, tributyltin carboxylate, or Ga(III)[OEP]Cl can be employed in other embodiments of this invention. In addition, in other embodiments, the chloride ion-exchange resin can be strong anion-exchange resin or weak anion-exchange resin, where the weak anion-exchange resin may comprise weak anion-exchange epoxy resin. The foregoing embodiment employs trimethyl ethenyl quarternary ammonium chloride polystyrene-divinylbenzene resin, whose structure provides free chloride ion that can exchange with chloride ions of the sample solution or the reference solution, as shown in FIG. 11. In other embodiments, any copolymer including trimethyl ethenyl quarternary ammonium anion-exchange group, m-phenylenediamine-formaldehyde resin, or melamine (acyl)-guanidine-formaldehyde resin can be used as the chloride-ion exchange resin.

In addition, the foregoing embodiment employs bis(2-ethylhexyl) sebacate ($C_{26}H_{50}O_4$, DOS) as the plasticizer, which makes the ion-selective membrane flexible, heat-resistant, light-resistant, and electrically insulated. Instead of DOS, 2-nitrophenyl n-octyl ether (o-NPOE) can be used as the plasticizer in another embodiment.

Accordingly, embodiments of this invention employ a chloride ion-exchange resin to replace conventional chloride ion-exchanger, and thus form a novel chloride ion-selective membrane, which is employed to produce a liquid-type chloride ion-selective electrode, which has been proven advantageous in quick response time, high sensitivity, and high accuracy, and because the chloride ion-exchange resin is anticorrosive, the developed chloride ISE has longer lifetime than conventional ISE.

Although specific embodiments have been illustrated and described, it will be appreciated by those skilled in the art that various modifications may be made without departing from the scope of the present invention, which is intended to be limited solely by the appended claims.

What is claimed is:

1. A chloride ion-selective electrode, for sensing the concentration of chloride ions of a sample solution, comprising:
    a reference electrode, immersed in a reference solution containing chloride ions; and
    a chloride ion-selective membrane, as an interface of the sample solution and the reference solution, comprising;
        a chloride ionophore, for binding chloride ions;
        a chloride ion-exchange resin, for exchanging chloride ions of the sample solution and the reference solution, wherein the chloride ion-exchange resin is selected from the group consisting essentially of strong anion-exchange resin, weak anion-exchange resin, and combinations thereof, and wherein the chloride ion-exchange resin is selected from the group consisting essentially of trimethyl ethenyl quarternary ammonium chloride polystyrene-divinylbenzene resin, m-phenylenediamine-formaldehyde resin, melamine (acyl)-guanidine-formaldehyde resin, and combinations thereof;
        a plasticizer; and
        a polymer matrix.

2. The chloride ion-selective electrode as recited in claim 1, wherein the chloride ionophore is selected from the group consisting of ({μ[4,5-dimethyl-3,6-bis(dodecyloxy)-1,2-phenylene]} bis(mercury chloride), bis-thiourea, tributyltin carboxylate, Ga(III)[OEP]Cl, and combination thereof.

3. The chloride ion-selective electrode as recited in claim 1, wherein the plasticizer is selected from the group consisting of bis(2-ethylhexyl) sebacate (DOS), 2-nitrophenyl n-octyl ether (o-NPOE), and combination thereof.

4. The chloride ion-selective electrode as recited in claim 1, wherein the polymer matrix is selected from the group consisting of polyvinyl chloride (PVC), polyethylene glycol (PEG), and combination thereof.

5. The chloride ion-selective electrode as recited in claim 1, wherein the weight ratio of the chloride ionophore to the chloride ion-exchange resin is about 99:1.

6. The chloride ion-selective electrode as recited in claim 1, wherein the weight ratio of the chloride ionophore, the plasticizer, and the polymer matrix is about 2:67:31.

7. The chloride ion-selective electrode as recited in claim 1, wherein the slope of the standard addition calibration curve of the chloride ion-selective electrode is consistent with the ideal Nernstian response of Nernst equation, and the linear correlation coefficient ($r^2$) of the standard addition calibration curve is more than 0.9910 and maintained till 70 days.

8. The chloride ion-selective electrode as recited in claim 1, wherein the limit of detection of the chloride ion-selective electrode is about 2.5 ppm.

9. The chloride ion-selective electrode as recited in claim 1, wherein the response time of the chloride ion-selective electrode is about 10 seconds.

10. The chloride ion-selective electrode as recited in claim 1, wherein the working pH range of the chloride ion-selective electrode is between about pH 2.0 and pH 11.0.

* * * * *